United States Patent
Dominick et al.

(10) Patent No.: US 10,620,919 B2
(45) Date of Patent: Apr. 14, 2020

(54) CREATING AND OPERATING SOFTWARE APPLICATIONS

(71) Applicant: SIEMENS HEALTHCARE GMBH, Erlangen (DE)

(72) Inventors: Lutz Dominick, Eggolsheim (DE); Vladyslav Ukis, Nürnberg (DE)

(73) Assignee: Siemens Healthcare GmbH, Erlangen (DE)

( * ) Notice: Subject to any disclaimer, the term of this patent is extended or adjusted under 35 U.S.C. 154(b) by 108 days.

(21) Appl. No.: 15/123,322

(22) PCT Filed: Mar. 6, 2014

(86) PCT No.: PCT/EP2014/054330
§ 371 (c)(1),
(2) Date: Sep. 2, 2016

(87) PCT Pub. No.: WO2015/131947
PCT Pub. Date: Sep. 11, 2015

(65) Prior Publication Data
US 2017/0075664 A1  Mar. 16, 2017

(51) Int. Cl.
*G06F 8/38* (2018.01)
*G06F 8/20* (2018.01)
(Continued)

(52) U.S. Cl.
CPC ............ *G06F 8/38* (2013.01); *G06F 8/20* (2013.01); *G06F 9/451* (2018.02); *G06Q 50/22* (2013.01); *G16H 40/20* (2018.01)

(58) Field of Classification Search
CPC ..... G06F 8/38; G06F 8/20; G06F 8/30; G06F 17/30896; G06F 17/3089; G06F 3/04842;
(Continued)

(56) References Cited

U.S. PATENT DOCUMENTS 7,356,606 B2 * 4/2008 Choate ................ G06F 17/2247
709/232
7,870,499 B2 * 1/2011 Latzina ................... G06F 9/451
715/763
(Continued)

FOREIGN PATENT DOCUMENTS

DE    102006033863 A1    1/2008
DE    102006051189 A1    5/2008

OTHER PUBLICATIONS

Dan R. Olsen, Jr.; Editing Templates a User Interface Generation Tool; IEEE; pp. 40-45; retrieved on Nov. 22, 2019 (Year: 1986).*
(Continued)

*Primary Examiner* — Ziaul A Chowdhury
*Assistant Examiner* — Cuong V Luu
(74) *Attorney, Agent, or Firm* — Lempia Summerfield Katz LLC

(57) ABSTRACT

A system for creating software applications and for operating these software applications on a plurality of different devices is provided. The system includes a number of functional units that may be repeatedly instantiated in the same application or in different applications, wherein each functional unit defines a delimited user interface (UI) area of a graphical user interface. Each functional unit has a specific part and a generic part. In this case, the specific part defines a number of UI elements having a predefined set of UI state variables. The generic part is set up to transform the values of the UI state variables into a device-independent and application-independent form and to export the values in this form as a state data record and to import such a state data record and to allocate the values contained therein to the UI state variables of the UI elements.

16 Claims, 4 Drawing Sheets

(51) Int. Cl.
*G06F 9/451* (2018.01)
*G16H 40/20* (2018.01)
*G06Q 50/22* (2018.01)

(58) Field of Classification Search
CPC ...... G06F 8/60; G06F 16/9535; G06F 16/972;
G06F 8/315; G06F 16/258; G06F 16/245;
G06F 11/324; G06F 16/00; G06F 16/116;
G06F 16/168
See application file for complete search history.

(56) References Cited

U.S. PATENT DOCUMENTS

| | | | | |
|---|---|---|---|---|
| 8,370,751 | B2* | 2/2013 | Graeff | G06F 8/38 715/744 |
| 9,497,313 | B2* | 11/2016 | Kinoshita | G06F 8/38 |
| 9,842,188 | B2* | 12/2017 | Stern | G06Q 10/10 |
| 2005/0204281 | A1* | 9/2005 | Choate | G06F 17/2247 715/234 |
| 2008/0141234 | A1* | 6/2008 | Becker | G06F 8/36 717/162 |
| 2008/0288877 | A1* | 11/2008 | Latzina | G06F 9/451 715/762 |
| 2008/0313353 | A1* | 12/2008 | Roediger | G06F 16/9577 709/246 |
| 2009/0063988 | A1* | 3/2009 | Graeff | G06F 8/38 715/744 |
| 2011/0035706 | A1* | 2/2011 | Kinoshita | G06F 8/38 715/835 |
| 2012/0191735 | A1* | 7/2012 | Duff | G06F 17/30303 707/756 |
| 2014/0019891 | A1* | 1/2014 | Borah | G06F 8/30 715/762 |
| 2014/0100885 | A1* | 4/2014 | Stern | G06Q 10/10 705/3 |
| 2015/0020006 | A1* | 1/2015 | Kotzer | G06F 3/0484 715/762 |
| 2015/0186603 | A1* | 7/2015 | Buckle | G06F 17/248 705/3 |

OTHER PUBLICATIONS

Debmh Hix; Generation of User Interface Management Systems; IEEE; pp. 77-87; retrieved on Nov. 22, 2019 (Year: 1990).*
Auman A.; GUI-Programmierung 2—Windows Presentation Foundation (WPF), TUM Seminar on Object-oriented Development, Munich, URL: http://www4.in.tum.de/lehre/seminare/ps/WS1011/oocs/download/aumann-pdf.pdf, pp. 1-15, XP055153361, 2010.
PCT International Search Report and Written Opinion of the International Searching Authority dated Nov. 27, 2014 for corresponding PCT/EP2014/054330, with English Translation.

* cited by examiner

FIG 2

| | |
|---|---|
| 1 | System |
| 2, 2a-d | (Software) application |
| 4 | Device |
| 9 | Personal computer (PC) |
| 10 | Screen |
| 11 | Tablet computer |
| 12 | Smartphone |
| 15 | State memory |
| 16 | Table storage |
| 17 | Public cloud |
| 20 | Frame component |
| 21 | Presentation layer |
| 22 | Business logic layer |
| 23 | Data repository layer |
| 24 | Runtime environment |
| 25 | Program library |
| 26 | Data model |
| 27 | State model |
| 28, 28a-e | Spike |
| Z | State data |

| 21 | Presentation layer | 28, 28a-e | Spike | 36 | Meta spikelet |
| 22 | Business logic layer | 30 | (Specific) part | 37 | Data spikelet |
| 23 | Data repository layer | 31 | (Generic) part | 38 | State spikelet |
| 24 | Runtime environment | 32 | UI element component | 39 | Handler spikelet |
| 25 | Program library | 33 | UI layout component | N | Payload data |
| 26 | Data model | 34 | UI function handler component | Z | State data |
| 27 | State model | 35 | Business logic component | | |

| 2 | (Software) application |
| 15 | State memory |
| 20 | Frame component |
| 32 | UI element component |
| 33 | UI layout component |
| 34 | UI function handler component |
| 35 | Business logic component |
| 36 | Meta spikelet |
| 37 | Data spikelet |
| 38 | State spikelet |
| 39 | Handler spikelet |
| 40-44 | Call |
| 50-59 | Event |

CREATING AND OPERATING SOFTWARE APPLICATIONS

The present patent document is a § 371 nationalization of PCT Application Serial Number PCT/EP2014/054330, filed Mar. 6, 2014, designating the United States, which is hereby incorporated by reference.

TECHNICAL FIELD

The embodiments relate to a system for creating software applications and also for operating these software applications on a plurality of different devices. In this regard, the system may be applicable to creating and operating software applications for processing medical data, e.g., for displaying and processing medical image data.

BACKGROUND

Medical workflows are increasingly implemented by incorporating a plurality of (e.g., data-processing) devices, e.g., computer-aided imaging modes such as computer tomographs or magnetic resonance tomographs, and also specialized computer systems. To support these complex workflows, a plurality of specialized (e.g., software) applications has developed with functional scopes that to some extent overlap and to some extent complement each other.

In addition to the conventional static data processing devices such as reporting stations, for example, compact mobile devices such as smartphones and tablet computers are also being employed to an increasing extent in medical practice, resulting in a further diversification of the applications and application variants to be provided.

These circumstances result in a user frequently changing application and/or device in the course of processing a medical workflow. However, a change in application or device of this type may be associated with a perceptible loss of efficiency (and therefore processing time), particularly as the user, following a change of this type, cannot as a rule continue directly at the point at which he previously exited the workflow. It is rather the case that the data linked to the workflow constantly has to be retrieved and loaded again. Furthermore, as a rule the settings of the respective application have to be set again to the requirements of the respective user and the workflow to be processed. Additionally, there is a risk, in the case of changes of application and device, of working results being lost because they are not properly stored and/or are not available promptly or correctly in the new application or the new device respectively.

A further problem that likewise results in losses in efficiency in medical workflows consists in the fact that the various applications and devices used in a workflow regularly require different operating methods and display a different operating behavior (that is to say a different response to comparable user interactions). Different applications therefore regularly have a different 'look & feel'. Consequently the user regularly has to operate different applications (including identically named applications on different devices) differently, which represents a high learning cost and causes operating errors.

A cause of the problems described in the foregoing includes the fact that applications and application variants largely have to be created independently of each other since the specific requirements for the various medical tasks, but also the various form factors of the devices used, stand in the way of a greater integration of medical software solutions.

The form factor may be characterized in this regard by the screen area and resolution available on a device that, in the case of the devices employed (such as workstations with a plurality of screens on the one hand and smartphones on the other), is extremely varied and consequently requires different solutions in the structuring of applications and their user interfaces.

As a rule, modern medical applications are constructed with multiple layers and therefore organized horizontally. Thus, in the case of an application of this type, the presentation logic that defines the user interface (UI) is separated from the so-called business logic (BL), e.g., the logic directed toward the actual task of the application.

An established paradigm for structuring applications with a graphical user interface is, furthermore, the so-called Model View ViewModel (MVVM) concept. According to this concept, the "view", that is to say the graphical elements on the user interface, is separated from the functioning of the user interface (the UI logic, also referred to as the "ViewModel"). This in turn is separated from the "Model", e.g., the data access layer for the payload data that is displayed to a user and processed. The ViewModel therefore represents an intermediary between the "View" and the "Model". The paradigms described above do indeed simplify, in general terms, the creation of applications, e.g., its high-level work component, yet do not offer any satisfactory solutions for the dilemma outlined above. Namely, on the one hand simple operation and creation of the many and varied medical applications and application variants may be made possible (which traditionally may only be achieved via the greatest possible standardization of the various applications and application variants). But, on the other hand, an individual adaptation of these applications and application variants to the respective purpose and the devices used has to be provided (which traditionally necessitates a diversification of the applications and application variants and therefore renders application operation and creation more difficult).

SUMMARY AND DESCRIPTION

The scope of the present invention is defined solely by the appended claims and is not affected to any degree by the statements within this summary. The present embodiments may obviate one or more of the drawbacks or limitations in the related art.

Disclosed herein is a system for creating software applications, (e.g., for processing medical data), and also for operating these software applications on a plurality of different devices.

The system makes available, as a central element, a number of delimited software structures (e.g., at least one software structure of this type, and in some instances, a plurality), each of these software structures being allocated a specific function. Consequently, these software structures are also referred to as "function units" or, for the purposes of a short and expressive designation, as "spikes" in the following.

In this regard, each of these spikes may be instanced repeatedly in various software applications, but optionally also repeatedly in one and the same software application. An "instance" of a spike in this regard is the designation used for an expression of that spike that forms part of a specific application, and is executed on a specific device, and is configured to those applications and also that device.

In this regard, each spike defines a delimited (UI) area of a graphical user interface (GUI). Optionally, the UI area allocated to a spike is highlighted visually on the graphical user interface by a frame, a window, a color block or similar in this regard. However, the boundaries of the UI area allocated to the spike do not necessarily have to be visually marked.

A spike may provide one of the following functions, for example: a UI window (image display segment) for displaying a digital medical image, a UI window that contains special functions for processing medical image data, e.g., a coherent (functionally autonomous) sub menu of an image display segment, a virtual control panel that includes setting controllers for setting image manipulation functions or for activating an imaging mode, a viewer for video files, a UI window that displays demographic data relating to a patient (e.g. name, patient identification number, address, date of birth, etc.), a UI window that presents a list of opened patient files or studies respectively or a worklist of tasks to be processed, or a search field.

In terms of its structure, each spike is organized in two parts, namely: a specific part that may be predefined differently for each instance of the spike (and therefore for each application and/or each device), and also a generic part that provides a device-independent and application-independent description, in a generalized form, of the internal state of every instance of a spike.

In this regard, the specific part defines, in a presentation layer, a number of UI elements, e.g., elements of a graphical user interface (GUI) having a predefined set of associated UI state variables. To this extent, the specific part of every spike is like the presentation layer of a conventional application.

The generic part of every spike is then set up to transform the values of the UI state variables in to a device-independent and application-independent form and to export said values in this form as a state data record. Furthermore, the generic part of every spike is also set up to import such a state data record and to allocate the values contained within it (where relevant following back-transformation in to the respectively matching device-specific and application-specific form) to the UI state variables of the UI elements of the specific part.

The generic part of every spike therefore forms a type of intermediary or adapter by way of which the various instances of the same spike may exchange their internal state across device and application boundaries. This transfer of a state enables a user to continue a workflow begun on a specific device and a specific application without a significant loss in efficiency or time following a change of device and/or application. The transfer of a state therefore results in the "feel" of the original application being transferred to another device and/or another application.

At the same time however, the external appearance (that is to say the "look") of each instance may be configured with the aid of the specific part of every spike to the specific circumstances and requirements of the respective device and the respective application; and, e.g., each instance of a spike may be configured to the form factor of the associated device by configuration of the specific part.

The user therefore benefits from the spikes made available in the context of the system to the effect that he may "take" the "feel" of a spike with which he is familiar from device to device and from application to application but in each case enjoys a "look" optimized to the respective device and the respective application.

Furthermore, the provision of the spike, which on the one hand may be reused in various applications, but on the other hand may also be configured to the respective application and the associated device also simplifies the creation of software applications.

At least one of the software applications building on the system may be organized horizontally in a plurality of layers, specifically at least one presentation layer and one business logic layer. Delimited from the presentation layer, which defines the graphical user interface of the application, and where relevant delimited from a data repository layer, for example a database, the business logic layer contains in this regard the business logic (BL) of the application, e.g., the logic relating to the actual task of the application and to a lesser extent the technical implementation.

Configured to this layer architecture, at least one of the spikes also includes a business logic layer, in addition to the presentation layer. A spike therefore extends as a rule across a plurality of layers of the application and therefore represents, within its architectural scheme, a vertical structure in contrast to the horizontal layers.

Each spike, to the extent that it includes business logic, is also organized in the specific part and the generic part at the level of the business logic. In this regard, the specific part includes, in the business logic layer, at least one business logic component that includes a number of BL state variables. Corresponding to its belonging to the specific part of the spike, a business logic component or each business logic component may have a different technical implementation in each instance of the spike. For example, the business logic component or each business logic component of a spike may be implemented in various programming languages for different instances of the spike. Nor do all business logic components of a spike have to be present in each of its instances. Instead, one or a plurality of business logic components of the spike may also be omitted in one instance of the spike, for example, if the functions implemented by this are irrelevant for the application or the device for which that instance is intended.

With reference to the business logic layer, the generic part of the spike is set up to transform the values of the BL state variables in to a device-independent and application-independent form and to export the values in this form as part of the state data record. Furthermore, the generic part of the spike is set up so as, during import of the state data record, to allocate the values of the BL state variables contained within it (where relevant following back-transformation in to the respectively matching device-specific and application-specific form) to the business logic component or each business logic component. The internal state of the business logic that is present where relevant may therefore also be transferred from one instance to another instance of the spike by the spike or each spike.

In an embodiment, it is not only the states, that is to say the values of the UI state variables and also where relevant the BL state variables, that are exported and imported by the spike or each spike. Instead, access information is also exported or imported respectively in conjunction with the state data record, which access information identifies the payload data used by the spike (or more precisely the exporting instance of the spike) at the time of export. Payload data refers in this regard to that data that is fundamentally independent of the respective spike and its technical implementation, and which is just used or processed by the spike. In the case of applications for deployment in the medical domain, the payload data constitutes in this regard the medical data, that is to say for example image data, patient data, task lists, medical reports, etc.

It is conceivable, e.g., in the case of small data records, that the exported or imported access information respectively contains the relevant payload data itself, that is to say that the payload data is exported and imported by value.

However, the access information may contain a reference to the memory location of the payload data in a data memory outside the application, based on which the spike (or more precisely, the importing instance of the spike) loads (e.g., automatically), the payload data following the import of the state data record.

Following a change of device or application, therefore, the user immediately has available not only the internal state of the respective spike but also the payload data previously used or processed by same, without the user having to search for and load that data again by deliberate interaction.

It is conceivable that the state data record is immediately transferred from one instance to another instance of the same spike. For the purposes of a simpler and more flexible handling of the applications building on the spike concept, the system includes however, in a departure from this, a central state memory in which the exported state data records are held in persistent form. The generic part of every spike is set up in this regard to export the state data record to this state memory. Furthermore, the generic part of every spike is also set up to access this state memory for the import of state data records.

This state memory may constitute any desired data memory that is accessible right across the system. The state memory may be implemented in a server-supported database. Given the worldwide availability, the virtually unconstrained scalability, and the high level of data security, however, the state memory may be implemented in a cloud storage facility, e.g., the cloud storage of a so-called public cloud (for example the service "Windows Azure" provided by the company Microsoft).

In an embodiment of the system, the generic part of every spike is not just used for collecting and transferring states and payload data. Instead, it additionally forms a model, which is abstracted from device-specific and application-specific details, of at least the presentation layer of the respective spike. For these purposes, the generic part of every spike in the presentation layer defines the UI state variables and also static properties of the UI elements in the form of abstracted, device-independent and application-independent (UI) default elements.

In this regard, the specific part of the respective spike determines the device-dependent and/or application-dependent concretized UI elements in conformity with the default elements. Each of the default elements defined in the generic part therefore forms an abstracted pattern or template filled out with a matching concrete UI element by the specific part of the respective spike. In this sense, "matching" means that the UI state variables of the concrete UI element have to be in conformity with the generalized UI state variables of the respective default element, so that the state of the default element may be "mapped" to the state of the concrete UI element and vice versa. In this regard, each concrete UI element has to be allocated a default element, and each UI state variable of every concrete UI element a generic UI state variable of the respective default element, but not necessarily vice versa. Fundamentally, therefore, the generic part of a spike may include default elements and UI state variables to which there is no concretized correspondence in the specific part of the same spike (e.g., of a specific instance of the same spike). Individual instances of a spike may concretize the abstracted UI model of the generic part in simplified form with a subset of concrete UI elements and/or fewer UI state variables.

For exporting and importing the internal state of the UI elements, the values of the UI state variables may be transferred reversibly in this regard between the concrete UI elements and the associated UI default elements, through corresponding transformation, in each instance of every spike.

Where a spike also includes business logic in addition to the presentation logic, the generic part of that spike may also contain a corresponding BL default element for each business logic component, which element mirrors the BL state variables of the respective business logic component in abstracted, namely device-independent and application-independent form.

The abstracted modeling of the presentation layer and where relevant the business logic layer of every spike by its generic part represents on the one hand an efficient and flexibly deployable tool for transferring the internal state of an instance of a spike to another instance across device and application boundaries. Furthermore, this concept enables a fundamental simplification during the creation of the software applications, particularly as, on the basis of the default elements being once defined, all instances of the spike—at least at the level of the presentation layer—may be generated completely, or at least virtually completely, automatically.

To enable a simple state transfer, all instances of a spike may bear a common name within the system, by which these instances may be unambiguously identified as belonging together.

The state data record exported by an instance of a spike is stored in the state memory, e.g., together with the name of the associated spike and also furthermore with at least one further item of data for indicating a specific workstep or project. The item or each further item of data may be: (1) the name or some other identification of a user; (2) a unambiguous designation for the exporting instance or, by way of a substitute, items of data relating to the device and the application to which that instance belongs; or (3) one or a plurality of data items relating to the medical workflow during the processing of which the state data record was generated, e.g., the name or the identification number of a patient, the designation of the workflow, the designation of the processed medical study according to DICOM, etc.

In this regard, the term "state data record" is to be understood in general terms in the sense of a collection of data that characterize the inner state of an instance of a spike (that is to say the values of the UI state variables, where relevant of the BL state variables, and also where relevant the payload data used). However, the state data record may be structured as desired in terms of its format and may also be organized in a plurality of independently exportable and importable sub data records.

The items of data deposited in the state memory together with the state data record make it possible for the user, following a change of device and/or application, to retrieve in a targeted manner that state data record relating to a workflow commenced prior to the change, and to import same for a seamless continuation of the workflow.

Each spike may be set up to export the internal state of every instance at predefined intervals automatically, without intervention by the user, for the purpose of generating a recover point in the state memory. On the one hand, this enables consistent production of the internal state of an application in the event of an error. On the other hand, the continuously repeated saving of the state also enables parallel processing of one and the same workflow on different devices and/or different applications.

BRIEF DESCRIPTION OF THE DRAWINGS

An exemplary embodiment is explained in detail below on the basis of a drawing.

FIG. 2 depicts a schematic representation of the software-related structure of the system with, by way of example, four applications operating on a total of three devices, each of the software applications being formed in each case out of a frame component and also instances of a number of function units (e.g., spikes), and instances of the same spike being set up to exchange their internal state by way of a state memory.

Parts and dimensions corresponding to each other are universally labeled with the same reference symbols in all figures.

DETAILED DESCRIPTION

Figure 1:
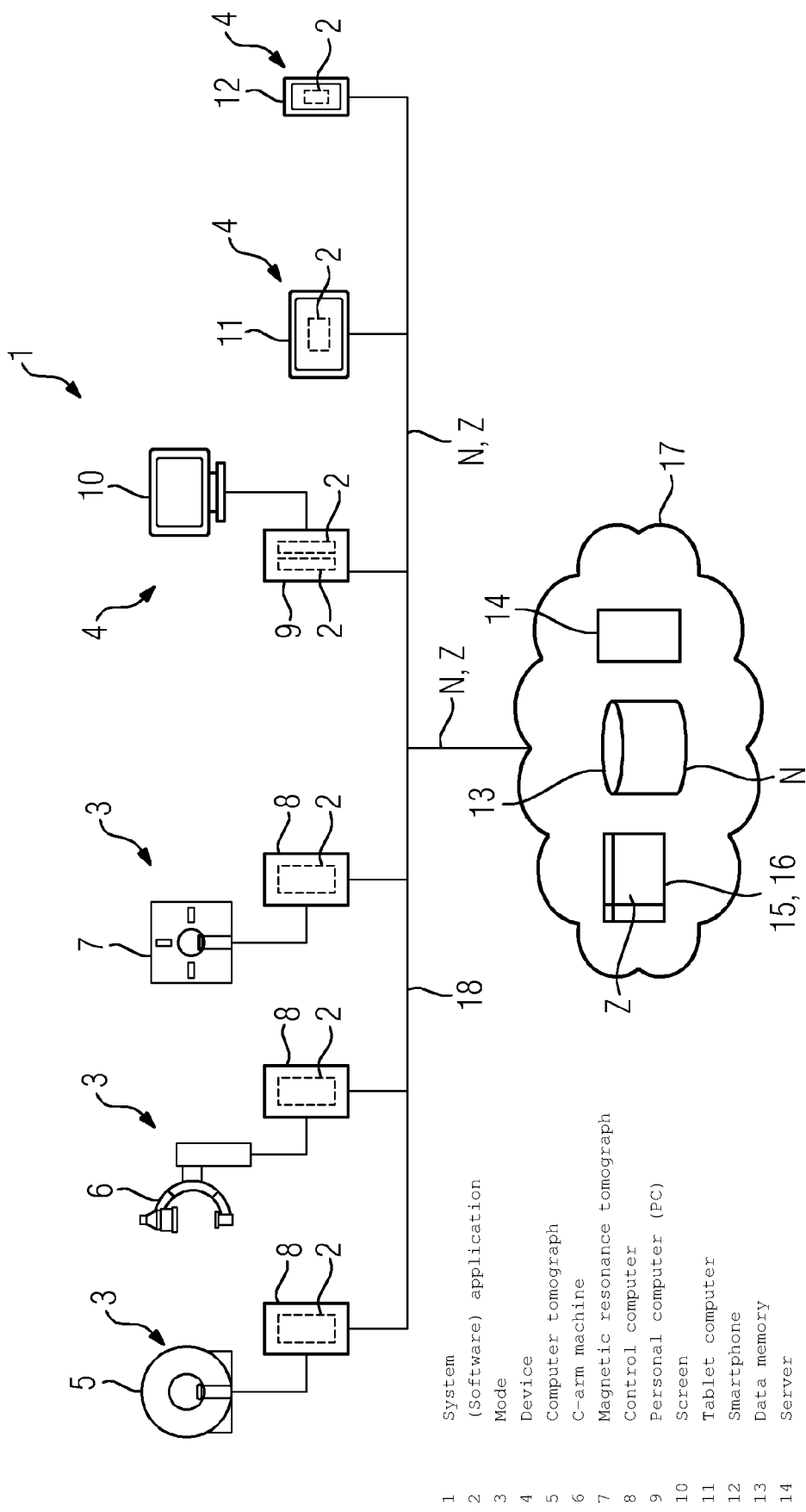
FIG. 1 depicts an example of a schematic block diagram of a system in which a plurality of software applications, which are set up to process medical data, are operated on a plurality of devices.

FIG. 1 depicts, in a rough schematic simplification, a system 1 for operating (e.g., software) applications 2, which are used for generating and processing medical data, on a plurality of devices. The devices of the system 1 on which the applications 2 are operated as intended include, on the one hand, medical imaging modes 3 for generating medical image data and also, on the other hand, user devices 4 for displaying and processing the image data and also other medical data.

A computer tomograph 5, a C-arm machine 6, and also a magnetic resonance tomograph 7 are represented by way of example in FIG. 1 as modes 3 of the system 1. In this regard, each of these modes 3 is allocated a control processor 8 on which at least one control software program is implemented as an application 2 for controlling an investigation undertaken by using the respective mode 3. Moreover, the control software allocated to the respective mode 3 includes, as a rule, functions for preparing and displaying the image data recorded.

The user devices 4 in the system 1 include, for example, workstations or personal computers 9 ("PCs") with a connected screen 10 in each case, but also modern mobile devices such as tablet computers 11, for example, and also smartphones 12. The applications 2 implemented on the user devices 4 for this purpose include, for example, software for reporting the medical image data, wherein this software may be present in various variants for different medical specialties in each case (e.g., oncology, cardiology, etc.), software for creating medical reports, software for managing patient data, etc.

The system 1 furthermore includes one or a plurality of data memories 13 for storing the medical payload data N (e.g., image data, patient data, worklists, etc.), and also one or a plurality of servers 14 that make available database-supported data management systems (e.g., hospital information systems (HIS), radiology information systems (RIS), picture archiving and communication systems (PACS), etc.) and other services.

Finally, the system 1 includes a state memory 15 for persistent storage of state data records Z, which describe the internal state of function units of the application 2 in the manner described in detail below.

In this regard, the state memory 15 is set up in a cloud storage facility, e.g., a so-called table storage 16 facility of a public cloud 17, in the example of the system 1 represented. The data memory 13 also, and the server or each server 14 may be set up in the public cloud 17. In this regard, the "Windows Azure" service provided by the company Microsoft may be used as the public cloud 17. However, public cloud services of other cloud operators may also be incorporated. As an alternative to the cloud-based implementation, however, the data memory 13, the server or each server 14, and the state memory 15 may also be realized in the context of a regular client-server solution.

The components of the system 1, that is to say the modes 3, the user devices 4, and the public cloud 17 (together with the data memory 13, the server or each server 14, and the state memory 15) are connected with regard to data transfer aspects by way of a (e.g., data communications) network 18. Where the system 1 is allocated to a medical institution, (e.g., a clinic), the network 18 may be formed by a wired and/or wireless Intranet, which is constructed for example in the form of a so-called local area network (LAN) on the basis of cabled Ethernet technology and/or as a cable-free wireless local area network (WLAN). Outside of delimited medical institutions, the network 18 is formed by the Internet.

The public cloud 17 may be connected to the other components of the system 1 by way of the Internet.

FIG. 2 depicts the structure of the system 1 with regard to software aspects in a schematically simplified layout diagram. Four applications 2 are depicted, which are designated in detail as applications 2a-2d. The applications 2a-2d run, by way of example, on a total of three user devices 4. Thus, the application 2a is running on the PC 9, while the application 2b is being executed on the tablet computer 11, and the applications 2c and 2d on the smartphone 12.

Each of the applications 2 includes a frame component 20. This frame component 20 is set up to load further components, which determine the actual functional scope and the technical implementation of the application 2. As may be seen from FIG. 2, these further components are arranged in two layers in terms of architecture, specifically a (presentation) layer 21 and also a (business logic) layer 22.

For the purpose of reading and writing the medical payload data N, all applications 2 access a data repository layer 23, which is implemented on the server or each server 14 and therefore outside the application 2.

In this regard, each of the layers 21 and 22 rests on a runtime environment 24 and also on a program library 25, these components of the respective application 2 being made available, for example, from a framework, e.g., middleware arranged between the operating system of the respective user device 4 and the application 2.

Furthermore, each of the applications 2 includes two further components in each case, both in the presentation layer 21 and also in the business logic layer 22, which components are designated as data model 26 and state model 27 respectively, and which define payload data and states (e.g., runtime states) at the application level.

The runtime environment 24, the program library 25, the data model 26, and the state model 27 therefore form, in each layer 21, 22 of every application 2, a base that is identical in terms of its structure for all layers 21, 22 and all applications 2 (even if the concrete technical implementation of the runtime environment 24 and the program library 25 may vary, and also, as a rule, does vary).

The components building on this base are then organized in a specific number of function units, which are referred to as spikes 28 below. In this regard, each spike 28 is structured such that it is coherent and consistent in terms of its functional scope, that is to say that on the one hand it has no compulsory functional dependency on other spikes 28 and therefore (seen in technical terms) is also capable of functioning alone, and that on the other hand it has a functional scope that is meaningful and adequate for performing the task envisioned for it. With respect to the functional scope of the spikes 28, that is to say in terms of the task envisioned for every spike 28, reference is made to the examples set forth above.

Each spike 28 is furthermore compulsorily allocated an allocated area of a user interface (UI) of the application 2. In the case of a regular graphical realization of the user interface, the spike 28 therefore emerges to the outside in the form of a window or frame or a menu for example.

Particularly since each spike 28 provides a part of the user interface, it is inserted in the presentation layer 21 of the associated application 2 in all cases. In contrast to the layers 21 and 22, however, the spikes 28 constitute vertical structures in the architecture of the respective application 2. Consequently, where business logic is attributable to the task area covered by a spike 28, that spike 28 also includes a part inserted in the business logic layer 22 in addition to the part inserted in the presentation layer 21. The parts of a spike 28 that belong together are correspondingly also represented over each other in the representation according to FIG. 2.

The application 2a therefore includes five spikes 28a-28e, of which the spikes 28a, 28b, 28d, and 28e extend over both the presentation layer 21 and also the business logic layer 22. Diverging from this, spike 28c has no business logic and therefore exists exclusively in the presentation layer 21.

Finally, each spike 28 may be instantiated repeatedly. In this regard, various instances, e.g., expressions of one and the same spike 28, may be operated in different applications 2 and/or on different modes 3 or user devices 4. Furthermore, a plurality of instances of one and the same spike 28 may also be present in the same application 2.

In this sense, in the exemplary representation according to FIG. 2: (1) the application 2b includes two further instances of the spike 28e; (2) the application 2c includes a further instance of each of the spikes 28b, 28c, and 28d; and (3) the application 2d includes a further instance of the spike 28a.

The spikes 28a-28d of the application 2a running on the PC 9 are therefore divided up into the two "leaner" applications 2c and 2d for operation on the smartphone 12, the spike 28a being operated in isolation in the dedicated application 2d.

As is only indicated in rough schematic terms in FIG. 2, all the instances of one and the same spike 28 work together to the extent that they may transfer their internal state in the form of the state data record Z from one instance to another. To do this, one instance of a spike 28 (in the example according to FIG. 2, the instance of the spike 28a running within the application 2a) transfers the state data record Z to the state memory 15, from which the state data record Z may be loaded at a later time by another instance (for example, the instance of the spike 28a running within the application 2d), for the purpose of importing the internal state.

In an embodiment, each instance of every spike 28 exports its internal state (in the form of a corresponding state data record Z in each case) to the state memory 15 not just upon closing of the associated application 2 or upon a corresponding user command, but also without the intervention of the user, at regular time intervals (e.g., 5 minutes). By this, the state data records Z collected in the state memory 15 may also be used for recovering the state of an application 2 following an error.

In the state memory 15, each state data record Z is stored together with: (1) the uniform and unambiguous name of the spike 28 within the system 1; (2) the name or some other identification of the user working with the spike 28 at the time of export; (3) an item of data relating to the exporting instance of the spike 28 (or as a substitute, a data item relating to the application 2 and the mode 3 or the user device 4 respectively, which are allocated to that instance); or (4) an item of data relating to the workflow processed by using the spike 28 at the time of export (for example, by specification of the patient name and/or a number for the investigated study).

Based on these items of data, the state data record Z may be searched for in the state memory 15 and imported at a later time, where relevant on another mode 3 or another user device 4 and/or from another application 2.

Figure 3:
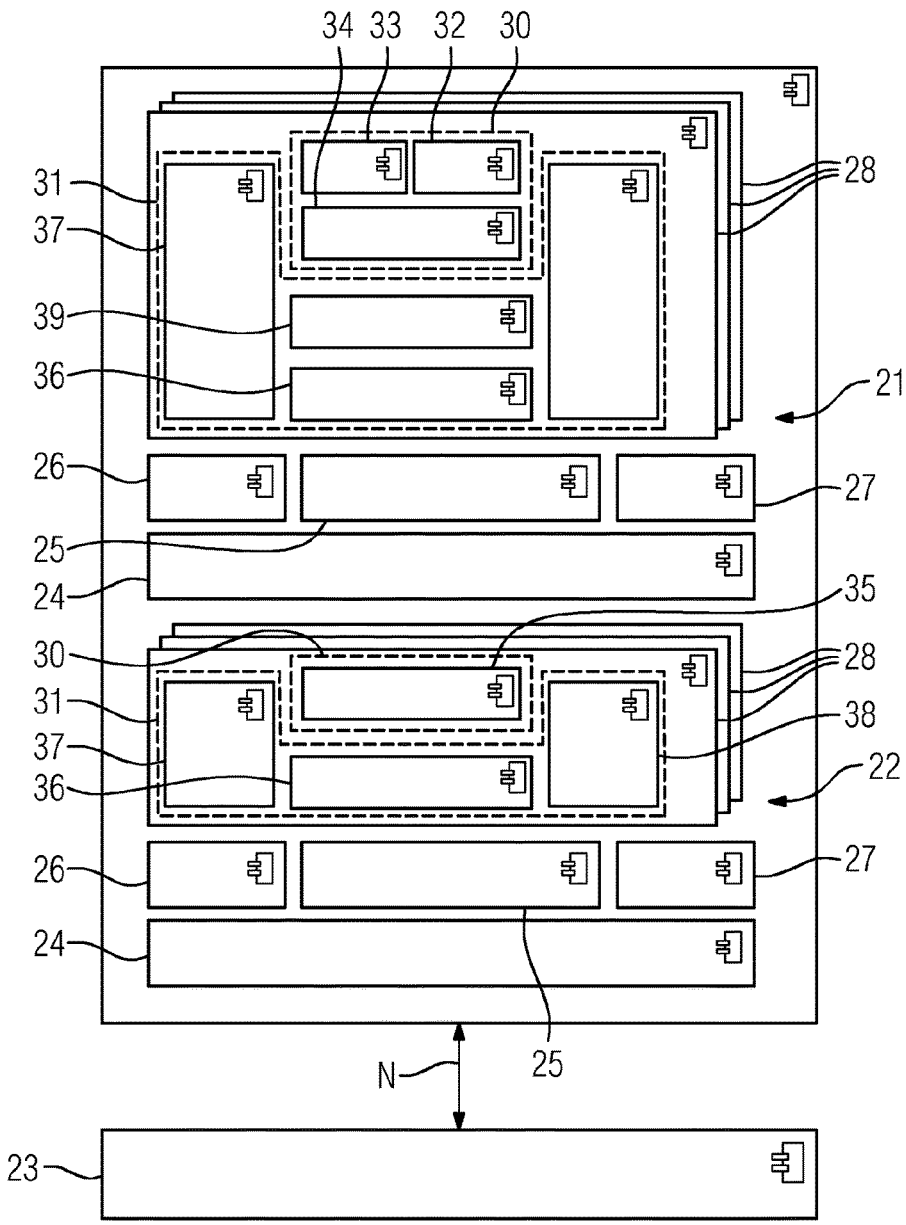
FIG. 3 depicts a representation according to FIG. 2 of an application of the system with a spike represented in greater detail.

In FIG. 3, the structure of a spike is represented in detail. According to this, each spike 28 includes a specific part 30 and also a generic part 31.

In this regard, the specific part 30 may be predefined specifically for each instance of the spike 28 so that the various instances of a spike 28 regularly differ in this specific part 30. In this regard, the specific part 30 includes the following components in the presentation layer 21:

A UI element component 32 that defines a specific set of concrete UI elements for the user interface of the application 2. In this regard, the UI elements include as a rule passive graphical elements (e.g., frames, blocks of color, lines, etc.), simple control elements (e.g., buttons, virtual slide or rotary controllers, check boxes, etc.), complex, and extending, control elements (e.g. selection menus in various graphical expressions, text input fields, and also output fields for text and/or graphics. In this regard, a UI element may also already include a combination of a plurality of individual UI elements. In this regard, the UI element component 32 defines static properties and UI state variables for each of the UI elements.

A UI layout component 33 that defines the arrangement, that is to say, the geometric distribution of the UI elements on the user interface of the application 2.

A UI function handler component 34 that implements the technical functioning of the UI elements (that is to say the UI logic).

Where the spike 28 extends in to the business logic layer 22, its specific part 30 there includes at least one business logic component 35 that implements the business logic, where present, of the spike 28.

In the generic part 31, the spike 28 includes the following components (which are also referred to as "spikelets" to delimit them from the components of the specific part 30):

In the presentation layer 21 and also where relevant also in the business logic layer 22, a meta-spikelet 36 in each case, which contains general information relating to the relevant spike 28, e.g., the name of the spike, a list of the components contained in the spike, a list of the layers 21, 22 over which the spike 28 extends, and information about the functional scope of the spike 28, that is say the task envisioned for the spike, for example in the form of one or a plurality of medical codes (e.g., according to DICOM, SNOMED, ICD-10 and/or LOINC). In this regard, the codes may specify e.g. the anatomical area or each anatomical area of application of the spike and/or the diagnostic or therapeutic method or each diagnostic or therapeutic method to which the spike is applicable. In this regard, the meta-spikelet 36 behaves like a regular UI element so that it may loaded as such a UI element by the frame component 20 of the application 2. Additionally, the function for accessing the state memory 15 is implemented in the meta-spikelet 36. The meta-spikelet 36 may therefore write state data records Z to the state memory 15 and read them out of the state memory 15 at the runtime of the application 2.

In the presentation layer 21 and also where relevant in the business logic layer 22, at least one data spikelet 37 in each case, which represents an adapter between the internal data model of the respective spike 28 and the data model 25 of the respective surrounding application 2 and therefore renders the spike 28 configurable to the differing, where relevant, data models 25 of various applications 2.

In the presentation layer 21 and also where relevant in the business logic layer 22, at least one state spikelet 38 in each case, which mirrors the UI state variables or BL state variable respectively in an abstracted device-independent and application-independent form.

In the presentation layer 21, at least one handler spikelet 39, which processes application-specific and device-specific events.

The state spikelet 38 of the presentation layer 21 may define, for each concrete UI element and layout, an abstracted UI default element with corresponding state variables which, however—in contrast to the UI state variables of the concrete UI elements—are compulsorily identical for each instance of the spike 28.

Examples of such UI default elements are:

A default element of the "button" type, which describes a generic function button. This default element has, for example, the generic UI state variables "Button_Value", which describes the switching state of the function button (e.g. "operated"=1; "not operated"=2), and also "Button_Dimmed_State", which describes the activation state of the function button (e.g., "active/operable"=1; "inactive/not operable"=0). In this regard, this default element may be concretized by function buttons of various graphical representation and/or technical implementation in the UI element component 32 in various instances of the spike 28, e.g., by a function button with a text label in one instance and by a function button with an iconographic marking in another instance.

A default element of the "slide" type, which describes a generic setting controller. This default element has the generic UI state variables "Slide_Value", for example, which describes the setting value of the setting controller (e.g. in the form of a floating point figure with a minimum value of 0 and a maximum value of 100), and also "Slide_Dimmed_State", which describes the activation state of the setting controller (e.g. "active/operable"=1; "inactive/not operable"=0). In this regard, this default element may be concretized by setting controllers of various graphical representation and/or technical implementation in the UI element component 32 in various instances of the spike 28, e.g., by vertical slide controllers, horizontal slide controllers, rotary controllers, etc.

A default element of the "SelectOneOfN" type, which describes a generic single selection (that is to say an element that enables a user to select exactly one option out of a plurality of options offered for selection), and which may be concretized e.g., by a drop-down menu, a series of so-called radio buttons, etc., in an instance of the spike 28.

A default element of the "SelectMOfN" type, which describes a generic multiple selection (that is to say an element that enables a user to select as many options as desired out of a plurality of options offered for selection), and which may be concretized, e.g., once again by a drop-down menu, a series of so-called check boxes, etc., in an instance of the spike 28.

A default field of the "TextInput" type, which characterizes a generic input field for alphanumeric characters.

Alongside the dynamic UI state variables, static properties, (e.g., colors and labels), may optionally also be predefined at least with respect to a few of the default elements.

Additionally, UI default elements relating to structures of the UI layout are also defined by the state spikelet 38 of the presentation layer 21. Examples of this are:

A default element "SquareWithUIElementTypes", which describes a generic rectangular UI area, which may be populated with UI elements. This default element has the UI state variable "Focus_State", for example, which describes whether the UI area is in the focus of the GUI and therefore may interact directly with the user. As a static property for example, this default element contains a list of UI default elements contained and also data relating to their arrangement. In this regard, this default element may be concretized by a window (that may be moved independently on the GUI), a frame (that cannot be moved independently on the user interface), a color block or a tab in the UI layout component 33 in various instances of the spike 28.

A default element "DIP (N,M)", which describes a generic N×M field of UI areas, and which may be concretized for example as a matrix-type or tabular arrangement of the UI areas but also alternatively, in the case of the screen area of the user device allocated to an instance being too small, as a stack of tabs or full-screen representations displayed as alternatives to each other.

During export of the internal state of a spike 28, the UI state variables of the concrete UI elements and UI layout structures are "mapped" by the state spikelet 38 to the generic UI state variables of the UI default elements. The transformation of the UI state variables needed for this may consist in a pure handover of values. For example, the generic UI state variable "Button_Value" takes the value "1" or "0" unchanged from a corresponding UI state variable of a concrete function button, it being possible for a different name to be assigned to the last-named UI state variable from one instance to the next depending on the technical implementation. However, the transformation of the UI state variables may also be associated with an adaptation of values. For example, the value of the generic UI state variable "Slide_Value" is normalized to the value range [0;100] for these state variables during the transformation. Where the allocated concrete setting controller is alterable between the values 0 and 1, for example, the value of that concrete setting controller is multiplied by a factor of 100 in the course of the transformation.

In a corresponding manner, the BL state variables of the business logic component or each business logic component 35 are also mapped to corresponding generic BL state variables of corresponding BL default elements, where relevant, by the state spikelet 38 of the business logic layer 22.

The values taken by the generic UI state variables are then transferred by the meta spikelet 36 to the state memory 15 as part of the state data record.

Conversely, during the import of the internal state of a spike 28, the generic UI state variables of the UI default elements are back-transformed by the state spikelet 38 to the UI state variables of the concrete UI elements and UI layout structures. Correspondingly, the generic BL state variables of the BL default elements, where relevant, are back-transformed by the state spikelet 38 to the BL state variables of the business logic component or each business logic component 35.

However, the UI or BL default elements respectively defined in the state spikelet 38 are not only used for state transfer during the runtime of the respective spike 28 but as early as during the creation of the application 2. The UI default elements may be used in this regard to generate the instances of a spike 28 at least largely automatically. To do this, concrete UI elements are selected from a program library, (e.g., by a services implemented in the public cloud 17), on the basis of predefined selection rules as a function of the mode 3 or the user device 4 respectively for which the instance to be generated is intended, and also in conformity with the UI default elements defined in the state spikelet 38.

Figure 4:
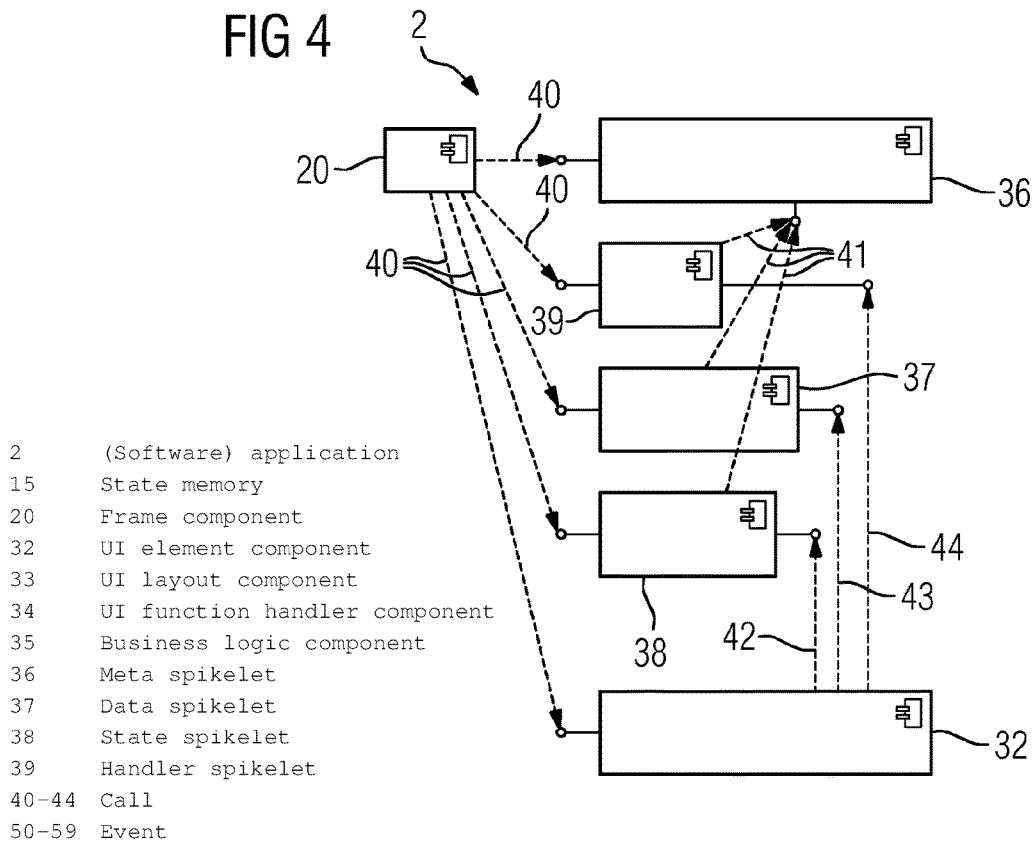
FIG. 4 depicts an example of a component diagram of the interaction between various components of the spike.

FIG. 4 depicts, in a component diagram, the interaction between the frame component 20 of one of the applications 2 and also various components of an instance 28 of a spike suspended in this application 2. It may be seen from the representation that the frame component 20 loads (by itself or by calling a loading routine) the meta spikelet 36, the handler spikelet 39, the data spikelet 37, the state spikelet 38, and also the UI element component 32 by calls 40. The meta spikelet 36 then accesses (in a manner not represented in detail) the state memory 15 and loads a state data record Z. Furthermore, the meta spikelet 36 loads the payload data N specified in the state data record Z.

The handler spikelet 39, the data spikelet 37, and the state spikelet 38 request from the meta spikelet 36, in calls 41, the relevant state information for the respective component and also further information. The data spikelet 37 may receive the payload data N loaded by the meta spikelet 36, e.g., the DICOM patient identification number and also demographic data relating to the patient, series, studies, and images according to the DICOM standard, and also data relating to medical findings. The state spikelet 38 receives the values of the generic UI state variables and transforms same back in to the respective device-dependent and application-dependent form.

The UI element component 32 fetches these back-transformed values from the state spikelet 38 in a call 42, and parameterizes the concrete UI elements (for example function buttons, image display segments, menus, and text input fields) correspondingly. The UI element component 32 furthermore accesses the data spikelet 37 and also the handler spikelet 39 in calls 43 and 44, in order to load payload data N or to call handlers respectively.

Figure 5:
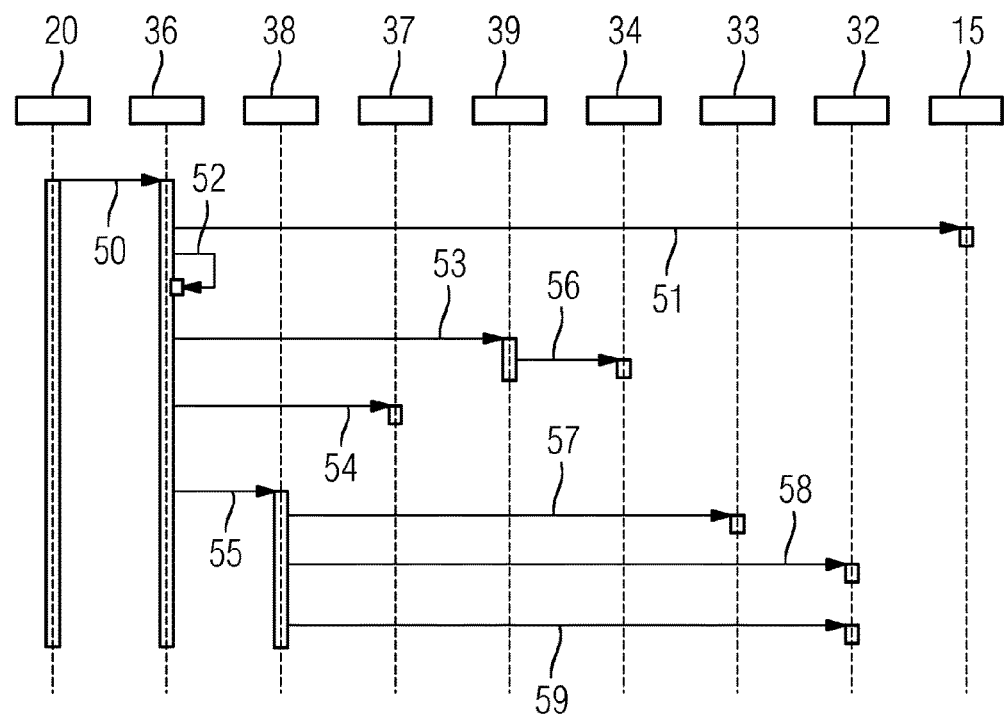
FIG. 5 depicts an example of a sequence diagram of the interaction between the frame component of an application, the state memory, and various components of a spike during import of the internal state previously exported by an instance of the same spike.

The time sequence upon starting an application 2 is represented in detail in FIG. 5. According to this, the frame component 20 loads the meta spikelet 36 as a regular UI element in a first event 50. The meta spikelet 36 then connects to the state memory 15 in order to load a state data record Z (event 51). In an event 52, the meta spikelet 36 first applies the loaded state data to itself. In the subsequent events 53, 54, and 55, the meta spikelet 36 transfers the respectively relevant part of the loaded state information to the handler spikelet 39, the data spikelet 37, and the state spikelet 38. The handler spikelet 39 in turn applies the loaded state data, in transformed form, to the UI function handler component 34 (event 56). The state spikelet 39 correspondingly applies the respectively relevant state information (that is to say the values of the UI state variables) in correspondingly transformed form to the UI layout component 33 and the UI element component 32 (events 57 and 58). In a final event 59, the state spikelet 38 selects a UI element in the manner specified by the state data record Z (and therefore analogously to the instance of the spike 28 that had exported the state data record Z previously).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A system for creating software applications and for operating the software applications on a plurality of different devices, the system comprising:

a central state memory separate from and in communication with the plurality of different devices; and a plurality of function units, wherein each function unit is configured to be repeatedly instantiated to form instances as a part of or in one and the same software application or a plurality of software applications executed on the plurality of different devices, wherein each function unit defines a delimited user interface (UI) area of a graphical user interface and a functional scope, wherein each instance of each function unit defines an expression of a particular device operating a particular software application, wherein each function unit comprises:

a specific part that defines, in a presentation layer, a number of UI elements having a predefined set of UI state variables, wherein the specific part is predefined differently for different devices and software applications and wherein the UI state variables of a first device or a first software application are configured to be retrieved or loaded by at least one second device or at least one second software application associated with the same function unit via the central state memory, and a generic part, wherein the generic part is configured: to transform values of the UI state variables of the first device or the first software application into a device-independent and application-independent form and to export the values of the UI state variables in the device-independent and application independent form as a state data record to the central state memory, and to import the state data record from the central state memory into the at least one second device or the at least one second software application and to allocate the values of the UI state variables contained within the state data record to the UI state variables of the UI elements so as to transform the values of the UI state variables back into a device-specific and application-specific form, wherein the state data record is configured to be exported to the central state memory by the first device operating the first software application and imported from the central state memory by the at least one second device operating the at least one second software application for a seamless continuation of a workflow associated with the state data record, and wherein the device-specific and application-specific form is adapted to the expression of the at least one second device or the at least one second software application by concretizing the UI elements according to the values of the UI state variables which have been transformed back into the device-specific and the application-specific form, and which have been retrieved or loaded by the at least one second device or the at least one second software application.

2. The system of claim 1, wherein the specific part of at least one function unit of the plurality of function units defines, in a business logic layer, at least one business logic component having a predefined set of business logic (BL) state variables, wherein the generic part is configured (1) to transform values of the BL state variables into a device-independent and application-independent form of the first device or the first software application and to export the values of the BL state variables in the device-independent and application-independent form as part of the state data record, and (2) to allocate, during the import of the state data record into the at least one second device or the at least one second software application associated with the same function unit, the values of the BL state variables contained within the state data record to the BL state variables of the business logic component or each business logic component so as to transform the values of the BL state variables back into a device-specific and application-specific form.

3. The system of claim 2, wherein the generic part of each function unit is configured to export, as part of the state data record, access information that identifies payload data used by the function unit at a time of the export operation, and to load, during the import of the state data record, the payload data identified based on the access information.

4. The system of claim 1, wherein the generic part of each function unit is configured to export, as part of the state data record, access information that identifies payload data used by the function unit at a time of the export operation, and to load, during the import of the state data record, the payload data identified based on the access information.

5. The system of claim 4, wherein the payload data comprises medical image data, patient data, medical reports, or combinations thereof.

6. The system of claim 1, wherein the state data record imported to the central state memory is deposited as a function of an importing function unit and as a function of at least one item of data for identifying a workstep carried out by using the importing function unit, so that the state data record is configured to be retrieved and imported in a device-independent and application-independent manner by each instance of the importing function unit by specifying the associated workstep.

7. The system of claim 6, wherein the central state memory is formed in a cloud storage facility of a public cloud.

8. The system of claim 1, wherein the generic part of each function unit defines, in the presentation layer, the state variables and static properties of the UI elements in a form of abstracted device-independent and application-independent default elements, wherein the specific part of the respective function unit specifies device-dependent and/or application-dependent concretized UI elements in conformity with the default elements, and wherein, in each instance of every function unit, the values of the state variables are configured to be transferred reversibly between the concrete UI elements and the associated default elements through a corresponding transformation.

9. The system of claim 1, wherein all instances of each function unit within the system are configured to be identified unambiguously as belonging together by a common name.

10. The system of claim 1, wherein the central state memory is formed in a cloud storage facility of a public cloud.

11. The system of claim 1, wherein a generic part of a function unit of the first device of the plurality of different devices is configured to export values of a state data record to the central state memory, and wherein a generic part of a function unit of the second device of the plurality of different devices is configured to import the values of the state data record from the central state memory.

12. The system of claim 1, wherein at least one function unit of the plurality of function units comprises a UI window displaying demographic data relating to a patient or a UI window displaying patient files.

13. The system of claim 1, wherein the delimited UI area of each function unit of the plurality of function units is highlighted visually on the graphical user interface by a window, frame, or color block.

14. The system of claim 1, wherein at least one function unit of the plurality of function units comprises a digital medical image.

15. The system of claim 1, wherein at least one function unit of the plurality of function units comprises a UI window having functions for processing medical image data.

16. The system of claim 1, wherein the plurality of devices comprise at least one medical imaging mode device configured to generate medical image data and at least one user device configured to display and process the medical image data.

* * * * *